US006767982B2

(12) United States Patent
Standke et al.

(10) Patent No.: US 6,767,982 B2
(45) Date of Patent: Jul. 27, 2004

(54) CONTINUOUS MANUFACTURING PROCESS FOR ORGANOALKOXYSILOXANES

(75) Inventors: Burkhard Standke, Loerrach (DE); Michael Horn, Rheinfelden (DE)

(73) Assignee: Degussa AG, Dusseldorf (DE)

(*) Notice: Subject to any disclaimer, the term of this patent is extended or adjusted under 35 U.S.C. 154(b) by 30 days.

(21) Appl. No.: 09/987,267

(22) Filed: Nov. 14, 2001

(65) Prior Publication Data
US 2002/0086907 A1 Jul. 4, 2002

(30) Foreign Application Priority Data
Nov. 14, 2000 (DE) .......................................... 100 56 343

(51) Int. Cl.$^7$ ............................ C08G 77/06; C07F 7/18
(52) U.S. Cl. ........................... 528/20; 528/10; 556/461; 556/470; 556/471
(58) Field of Search ..................... 528/10, 20; 556/466, 556/470, 471

(56) References Cited

U.S. PATENT DOCUMENTS

| | | | |
|---|---|---|---|
| 3,668,180 A | * 6/1972 | Brennan et al. | ............... 528/14 |
| 3,792,071 A | 2/1974 | Nitzsche et al. | |
| 3,846,358 A | * 11/1974 | Roedel | ........................ 524/773 |
| 4,226,793 A | 10/1980 | Kotzsch et al. | |
| 4,298,753 A | * 11/1981 | Schinabeck et al. | ........ 556/415 |
| 4,506,087 A | 3/1985 | Fischer et al. | |
| 5,112,393 A | 5/1992 | Engel et al. | |
| 5,527,937 A | 6/1996 | Standke et al. | |
| 5,536,860 A | 7/1996 | Monkiewicz et al. | |
| 5,543,173 A | 8/1996 | Horn, Jr. et al. | |
| 5,629,400 A | 5/1997 | Standke et al. | |
| 5,646,325 A | 7/1997 | Monkiewicz et al. | |
| 5,679,147 A | * 10/1997 | Standke et al. | ........ 106/287.11 |
| 5,808,125 A | 9/1998 | Standke et al. | |
| 5,849,942 A | 12/1998 | Standke et al. | |
| 5,863,509 A | 1/1999 | Standke et al. | |
| 5,885,341 A | 3/1999 | Standke et al. | |
| 5,932,757 A | 8/1999 | Standke et al. | |
| 6,084,116 A | 7/2000 | Horn et al. | |
| 6,177,582 B1 | 1/2001 | Jenkner et al. | |
| 6,177,584 B1 | 1/2001 | Loewenberg et al. | |
| 6,228,936 B1 | 5/2001 | Standke et al. | |
| 6,239,194 B1 | 5/2001 | Standke et al. | |
| 6,251,989 B1 | 6/2001 | Edelmann et al. | |
| 6,255,516 B1 | 7/2001 | Jenkner et al. | |
| 6,288,256 B1 | 9/2001 | Standke et al. | |
| 6,361,871 B1 | 3/2002 | Jenkner et al. | |
| 6,395,858 B1 | 5/2002 | Mack et al. | |
| 6,403,228 B1 | 6/2002 | Mack et al. | |
| 6,491,838 B1 | 12/2002 | Standke et al. | |
| 6,500,883 B1 | 12/2002 | Mack et al. | |
| 6,528,585 B1 | 3/2003 | Standke et al. | |
| 6,534,667 B1 | 3/2003 | Standke et al. | |

FOREIGN PATENT DOCUMENTS

| | | |
|---|---|---|
| DE | 27 44 726 | 4/1979 |
| DE | 28 09 871 | 9/1979 |
| EP | 0 518 057 | 12/1992 |
| EP | 0 579 453 | 1/1994 |
| EP | 0 650 968 | 5/1995 |
| EP | 0 814 110 | 12/1997 |
| GB | 674 137 | 6/1952 |

OTHER PUBLICATIONS

J. K. Crandall, et al., Journal of Organometallic Chemistry, vol. 489, pp. 5–13, "Siloxanes From The Hydrolysis Of Isopropyltrimethoxysilane", 1995.

* cited by examiner

Primary Examiner—Jeffrey B. Robertson
(74) Attorney, Agent, or Firm—Oblon, Spivak, McClelland, Maier & Neustadt, P.C.

(57) ABSTRACT

A mixture of organoalkoxysiloxanes of formula I:

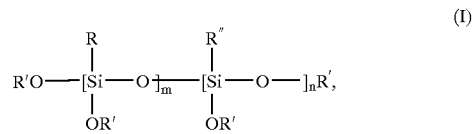

wherein R and R" are identical or different and are methyl, ethyl, vinyl, n-propyl, i-propyl, γ-chloropropyl, n-butyl, i-butyl, n-pentyl, i-pentyl, n-hexyl, i-hexyl, n-heptyl, i-heptyl, n-octyl, i-octyl, hexadecyl, octadecyl or alkoxy, R' represents methyl or ethyl, n and m are identical or different and each is 0 or an integer ranging from 1 to 20, on the condition that (n+m)≧2, is prepared by:
  reacting in a first stage the constituents of (i) an organotrichlorosilane or a mixture of organotrichlorosilanes or a mixture of at least one organotrichlorosilane and tetrachlorosilane, (ii) water and (iii) alcohol, combined in a molar ratio (i):(ii):(iii) of 1:(0.59 to 0.95):(0.5 to 100), at a temperature of 0 to 150° C., which produces hydrogen chloride as a product which is removed from the system and the crude organoalkoxysiloxane product is transferred proportionately to the reaction distillation column of a subsequent second stage after an average dwell time of 0.5 to 180 minutes; and
  conducting reaction and distillation in the reaction distillation column in a second stage in which volatile constituents are withdrawn from the top of the column and the organoalkoxysiloxane product is withdrawn as a bottom product, wherein the reaction-distillation column is operated at a bottom temperature of 50 to 200° C.

20 Claims, 1 Drawing Sheet

CONTINUOUS MANUFACTURING PROCESS FOR ORGANOALKOXYSILOXANES

BACKGROUND OF THE INVENTION

1. Field of the Invention

The present invention relates to organoalkoxysiloxanes, including mixtures of organoalkoxysiloxanes, to a process for manufacturing the organoalkoxysiloxanes and to the use of such mixtures.

2. Description of the Background

It is well-known to manufacture an organoalkylsilane by the esterification of an organochlorosilane with an alcohol.

It is also well-known to manufacture orthosilicic acid tetraalkylesters or their oligomers by esterification of tetrachlorosilane or oligomeric chlorosiloxanes, as described in DE 27 44 726 C2. In this process oligomerization can be performed by the addition of water in precise amounts simultaneously with esterification or in conjunction with esterification.

Because of the various hydrolysis or condensation characteristics of the monomeric educt and the resulting derivatives, control of the reaction for the production of oligomeric silicic acid esters is extremely difficult, in particular if the objective is to conduct esterification, hydrolysis and condensation simultaneously or continuously, particularly on the industrial scale. In addition, such systems should be as stable during storage as possible. That is, both physical and chemical properties such as oligomer distribution and viscosity should be maintained for as long as possible.

DE 28 09 871 C2 discloses a process for partial hydrolysis of orthosilicic acid tetra(alkoxyalkyl)ester, wherein the total quantity of water required for the desired extent of partial hydrolysis is already mixed in with the ester at the beginning of conversion.

EP 0 518 057 proposes a process for the production of organoalkoxysilanes by condensation or cocondensation of vinyl and/or alkylalkoxysilanes in the presence of a catalyst, wherein the calculated quantity of water is added in solution to the 0.2 to 8 times weight of methanol or ethanol.

EP 0 814 110 A1 (O.Z. 5063) also describes a process for the discontinuous production of $C_3$ to $C_8$-alkyltrialkoxysiloxanes by the condensation of corresponding alkylalkoxysilanes in the presence of hydrogen chloride (HCl), wherein more than 1 mol water per mol silicon is used for hydrolysis or condensation of the alkoxysilane.

EP 0 579 453 A2 proposes a process for manufacturing alkylalkoxysiloxanes, in particular, based on isobutyltrimethoxysilane (IBTMO), wherein 0.1 to 0.6 mol water per mol alkoxysilane is used for the objective hydrolysis. The result here is mixtures containing alcohols, in turn containing a high proportion of silane monomer, that is, educt, as a result of which the product exhibits a high proportion of volatile monomer when applied and which also has a low flash point.

A discontinuous method for the hydrolysis of isopropyltrimethoxysilane is also disclosed in J. Organometallic Chem. vol. 489 (1995).

U.S. Pat. No. 5,112,393 (WO 92/06101) discloses solvent-free organoalkoxysiloxanes having 2 to 9 Si units for the water-repellent coating of mineral building materials, wherein fluororganic compounds can be added to the siloxane in order to improve the repelling properties of the coating. U.S. Pat. No. 5,112,393 discloses $C_1$ to $C_{30}$-alkyl/cycloalkyl/arylalkyl/alkaryl or their mixtures as organo groups, and also olefinic organo groups and such groups substituted by heteroatoms or fluorine. Particular emphasis is given to siloxanes with $C_4$ to $C_8$-alkyl groups and an oligomerization degree of 2 to 4, wherein 1,3-di-n-octyl-1, 1,3,3-tetramethoxydisiloxane and 1,3-di-n-octyl-1,1,3,3-tetraethoxydisiloxane are preferred. They, too, are manufactured discontinuously. In addition, the objective manufacture of these disiloxanes is expensive.

A method for the specific hydrolysis of alkoxysilanes is also known as disclosed in U.S. Pat. No. 5,543,173, wherein the product results in a substantial amount of alcohol by the hydrolysis reaction or considerable quantities of solvents such as toluene or methylisobutylketone (MIBK). U.S. Pat. No. 5,543,173 discloses, as educts, organoalkoxysilanes with organo groups such as aminoalkyl, diaminoalkyl, for example, N-2-aminoethyl-3-aminopropyl, vinyl, $C_6$ to $C_{20}$-alkyl, for example methyl, ethyl, i-propyl, n-butyl, in particular octyl, halogenoalkyl, methacryloxyalkyl or mercaptoalkyl. Here, too, alkoxysilanes which are prepared in a separate process by esterifying the respective chlorosilanes with an alcohol are used. Such discontinuous processes performed over several processing stages are as a rule expensive and cost-intensive.

It should also be emphasized that each of these organoalkoxysilanes, including the corresponding oligomeric siloxanes, has a different hydrolysis or condensation behavior which, accordingly, considerably complicates such processes being conducted on a production scale.

SUMMARY OF THE INVENTION

Accordingly, one object of the present invention is to provide a highly economical process for the continuous manufacturing of organoalkoxysiloxanes.

Briefly, this object and other objects of the present invention as hereinafter will become more readily apparent can be attained by a process for the continuous manufacture of a mixture of mixture of organosiloxanes of formula I

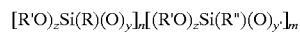

wherein R and R" are identical or different and are methyl, ethyl, vinyl, n-propyl, i-propyl, γ-chloropropyl, n-butyl, n-pentyl, i-pentyl, n-hexyl, i-hexyl, n-heptyl, i-heptyl, n-octyl, i-octyl, hexadecyl, octadecyl or alkoxy, R' represents methyl or ethyl, n and m are identical or different and each is 0 or an integer ranging from 1 to 20, on the condition that (n+m)≧2, y and y' are >0 to 1.5 and z and z' are 0 to <3, wherein y and y' and z and z' are the same or different, and (2y+z)=3 and (2y'+z)=3, comprising:

reacting in a first stage (i) organotrichlorosilane or a mixture of organotrichlorosilanes, preferably alkyltrichlorosilanes, in particular n-propyltrichlorosilane and/or vinyltrichlorosilane or a mixture of at least one organotrichlorosilane and tetrachlorosilane, (ii) water, appropriately demineralized water and (iii) alcohol preferably methanol and/or ethanol in a molar ratio (i):(ii):(iii) of 1:(0.59 to 0.95):(0.5 to 100), preferably 1:(≧0.6 to 0.9):(1 to 3), particularly preferably 1:(0.65 to 0.85):(1 temperature of 0 to 150° C., preferably from 20 to 70° C., particularly preferably at 40 to 60° C., which produces hydrogen chloride as a gaseous product which is removed from the system and the crude organoalkoxysiloxane product is transferred proportionately to the reaction distillation column of a subsequent second stage by way of a preheater, if required, after an average dwell time of 0.5 to 180 minutes, preferably 1 to 60 minutes, particularly preferably 4 to 30 minutes in order to complete the reaction in the column, with the optional supply of an additional quantity of alcohol in a molar ratio of (i):(iii) of 1:(0.1 to 100), preferably 1:(0.5 to 10), particularly preferably 1:(1 to 3), is supplied; and conducting reaction and distillation in the reaction distillation column in a second stage in which volatile constituents are withdrawn from the top of the column and the organoalkoxysiloxane product is withdrawn as a bottom product, wherein the reaction-distillation column is operated at a bottom temperature of 50 to 200° C., preferably 100 to 180° C., particularly preferably 150 to 170° C.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

the FIGURE is a schematic of the process and apparatus of the invention.

DETAILED DESCRIPTION OF THE PREFERRED EMBODIMENTS

Figure 1:
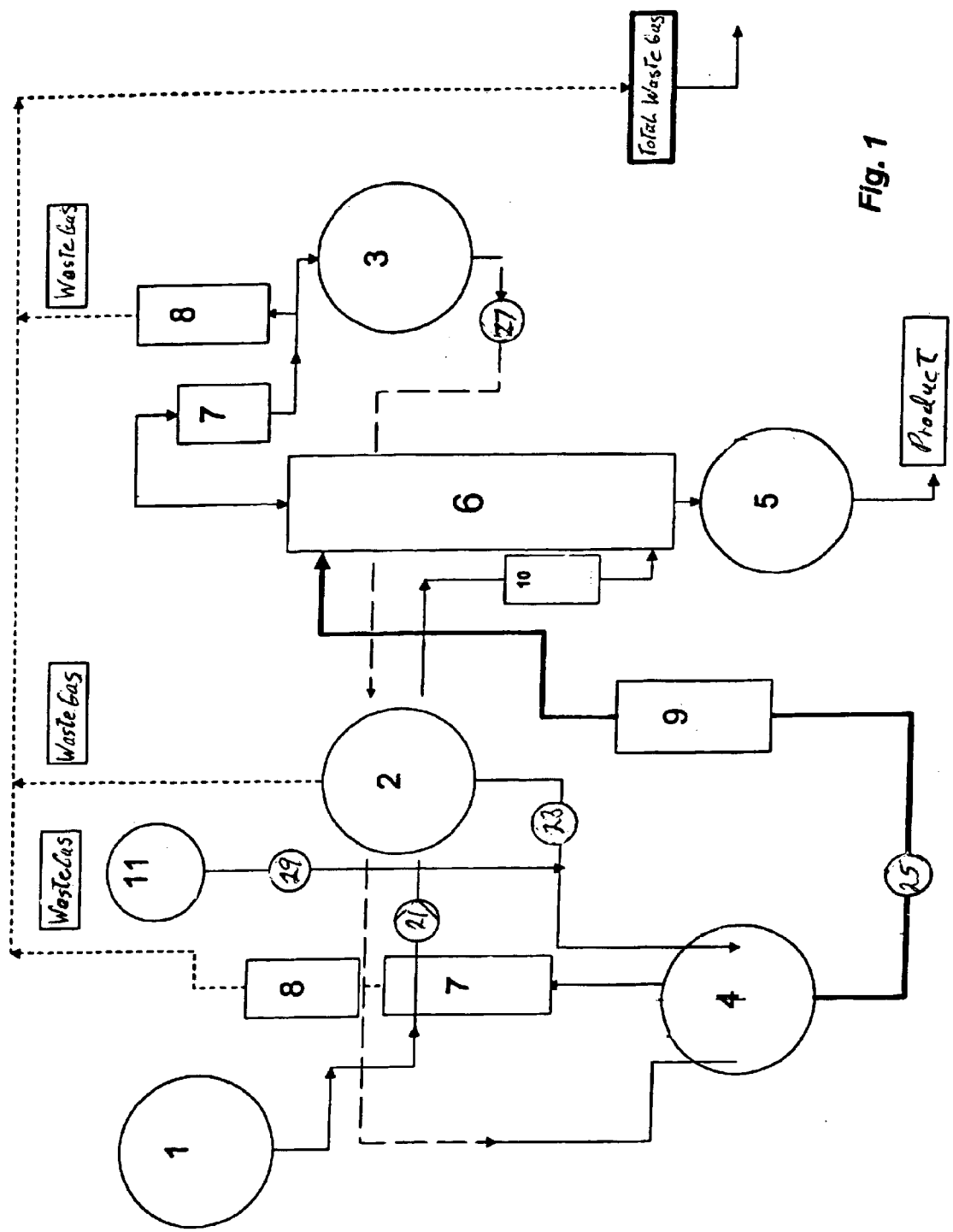

In particular, the organoalkoxysiloxanes of the invention can be manufactured easily and economically, and thus advantageously industrially, from an organochlorosilane or from a mixture of chlorosilanes, a defined quantity of water and an alcohol in a continuous process. In the first stage the educts are charged in a quantity similar to the product removed from the second stage, or, respectively, waste gas such as HCl and minimal quantities of chloralkyl are removed.

In a preferred embodiment of the continuous process a mixture of organosiloxanes of formula I:

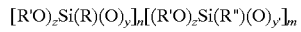

wherein R and R'' groups are identical or different and are methyl, ethyl, vinyl, n-propyl, ipropyl, γ-chloropropyl, n-butyl, n-pentyl, i-pentyl, n-hexyl, i-hexyl, n-heptyl, i-heptyl, n-octyl, i-octyl, hexadecyl, octadecyl or alkoxy, that is, methoxy or ethoxy for example, R' represents a methyl or ethyl group or optionally a hydrogen atom, n and m are identical or different and represent a number from 0 to 20, on the condition that (n+m)≧2, y and y' are >0 to 1.5, z and z' are 0 to <3, wherein y and y' and z and z' are the same or different, and (2y+z)=3 and (2y'+z')=3, is prepared by reacting, in a first process stage, (i) an organotrichlorosilane or a mixture of organotrichlorosilanes or a mixture of at least one organotrichlorosilane and tetrachlorosilane, (ii) water and (iii) alcohol combined in a molar ratio (i):(ii):(iii) of 1: (0.59 to 0.95):(0.5 to 100), at a temperature of 0 to 150° C., which produces hydrogen chloride as a product which is removed from the system and the crude organoalkoxysiloxane product is transferred proportionately to the reaction distillation column of a subsequent second stage after an average dwell time of 0.5 to 180 minutes; and conducting reaction and distillation in the reaction distillation column in a second stage in which volatile constituents are withdrawn from the top of the column and the organoalkoxysiloxane product is withdrawn as a bottom product, wherein the reaction-distillation column is operated at a bottom temperature of 50 to 200° C.

Another aspect of the present invention is mixtures of linear, cyclic and/or net-like organoalkoxysiloxanes of formula I, which can be obtained by the process of the present invention. Linear, cyclic and/or net-like organoalkoxysiloxanes are understood here in particular to mean structures having an average oligomerization degree of 2 to 30, preferably from 3 to 8, particularly preferably from 4 to 6.

In addition, the mixture of organoalkoxysiloxanes obtained as a bottom product upon distillation in the present continuous process may optionally contain a lesser or still measurable amount of monomeric organoalkoxysiloxane.

The following compounds are preferably used in the process of the present invention as chlorosilanes:tetrachlorosilane, methyltrichlorosilane, vinyltrichlorosilane (VTCS), ethyltrichlorosilane, n-propyltrichlorosilane (n-PTCS), i-propyltrichlorosilane (i-PTCS), γ-chloropropyltrichlorosilane, i-butyltrichlorosilane (i-BTCS), n-butyltrichlorosilane (n-BTCS), pentyltrichlorosilane, hexyltrichlorosilane, heptyltrichlorosilane, n-octyltrichloro-silane (n-OCTCS), i-octyltrichlorosilane (i-OCTCS), hexadecyltrichlorosilane and octadecyltrichlorosilane.

Methanol or ethanol is preferably used as constituent (iii).

In the process of the present invention the constituents (i), (ii) and (iii) are employed in the first process stage in a mole ratio of preferably 1:(≧0.6 to 0.9):(1 to 3), in particular in a mole ratio of 1:(0.8 to 0.85):(1.5 to 2.5).

The average dwell time of the constituents in the first process stage of the present invention is 0.5 to 180 minutes, preferably 1 to 60 minutes, particularly preferably 4 to 30 minutes, wherein the first process stage is operated at a temperature of 20 to 70° C., in particular 40 to 60° C.

Following the average dwell time the reaction generally reaches a stage in which it is possible to transfer the crude product proportionately, that is, continuously, from the first process stage to the reaction-distillation column of the second process stage. In doing so, the crude product from the first process stage can be fed to a preheater before it is introduced to the second process stage.

It is an advantage if the crude product is fed from the first process stage to the upper half of the reaction-distillation column. However, the crude product of the first stage can be fed to the lower section of the column of the second stage.

With respect to obtaining as complete an esterification as possible, a further advantage of the present process is the supply of alcohol, when the organotrichlorosilane or mixtures thereof (i) to alcohol (ii) molar ratio is 1:(0.1 to 100), to the lower section of the reaction distillation column of the second process stage.

At the same time the excess alcohol in the present process suitably accumulates at the top of the column as an alcohol fraction in the second process stage of the process of the invention.

FIG. 1 is a flow chart of a preferred embodiment of the present invention.

In general, the process of the present invention is conducted in such a way that the chlorosilane constituent (i) 2, water constituent (ii) 11 and alcohol constituent (iii) 1 are metered at the supply points shown and supplied to reactor 4 of the first process stage where they react at a reaction temperature of 0 to 150° C. with thorough mixing. After an average dwell time of 0.5 to 180 minutes, crude product is removed proportionately, that is, continuously, from the reactor 4 of the first stage while correspondingly fresh constituents (i), (ii) and (iii) are added to the reactor. The alcohol normally charged in excess can take on the task of a reaction constituent as well as that of a reaction medium. HCl resulting from conversion in the first reaction stage advantageously can have a catalytic effect during hydrolysis, esterification and condensation in the present process and is generally withdrawn as waste gas via the gas phase. The crude product removed continuously from the first stage is preferably fed to a preheater 9 and transferred to reaction distillation column 6 of the second process stage, wherein the desired product, that is, the mixture of organoalkoxysiloxanes is removed from column bottom 5 as product and the constituents foreign to the product can be essentially withdrawn via the top of the column at coolers 7 and 8.

In a preferred embodiment of the continuous process of the present invention the crude product can be conveyed from the first stage 4 into the upper section of the reaction distillation column 6 of the second stage and an additional quantity of alcohol can be supplied by way of evaporator 10 to the lower section of the reaction-distillation column 6 of the second stage, wherein chlorosilanes and chlorosiloxanes present in the crude product react with alcohol in counterflow while HCl is separated. Alcohol 3, accumulating in the second process stage at the column top and which after reaction may contain HCl, organochloroalkoxysilanes, organotrialkoxysilanes or the corresponding siloxanes, is fed back to column 6 of the second process stage following condensation and/or returned as educt to reactor 4 of the first process stage.

The bottom product from the second process stage of the process of the present invention may additionally undergo secondary treatment. Thus, if required, monomeric organoalkoxysilanes, traces of alcohol or organochlorosilanes still present in the bottom product can be removed from the product by distillation by means of another distillation unit downstream from the reaction-distillation column or by a thin-layer evaporator. Additionally, the organoalkoxysilanes of formula I that are present should contain at least one R or R" group that is different from alkoxy. Turbidities or suspended matter can be removed appropriately by filtration of the product. If it is desired to reduce the color index of the product, such can be done by treating the product with an absorptive substance such as active carbon or silica. The chloride content of the organoalkoxysilane mixture can also be further reduced by precipitation with an alkali such as sodium alcoholate, ammonia or caustic soda solution or potash lye.

According to the process of the present invention mixtures of n-propylmethoxysiloxanes, n-propylethoxysiloxanes, vinylethoxysiloxanes, vinylmethoxysiloxanes or correspondingly mixed—propyl/vinylsiloxane copolymers are particularly preferably manufactured. These products are characterized in particular by a special composition of the oligomer mixture with an average oligomerization degree of 2 to 30, preferably from 3 to 8, particularly preferably from 4 to 6, as also taught, for instance, in the corresponding German application entitled "n-Propylethoxysiloxanes, Process for their Manufacture and Use". It is pointed out expressly that the corresponding German application entitled "n-Propylethoxysiloxanes, Process for their Manufacture and Use" discloses the content of the present application.

Mixtures of polycondensed, preferably oligomeric organoalkoxysilanes, obtained by the present process are as a rule solvent-free and stable in storage for more than 6 months and can be used advantageously as a concentrate, in diluted form, for instance, dissolved in petroleum hydrocarbons or as an alcoholic solution, preferably dissolved in methanol, ethanol and/or in n-propanol or isopropanol, or in emulsified form, preferably as an aqueous preparation both in low-viscosity and high-viscosity paste-like state, or in any media whatsoever. In this way the organoalkoxysiloxane mixtures of the present invention can be used in an aqueous and/or alcoholic preparation with the addition of a thickening agent for generating paste-like properties for the treatment of inorganic surfaces, such as for water-, oil-, dirt- or dye-repellent or corrosion-inhibiting or adhesion-promoting treatment of metal, ceramic, building materials, building components and buildings, such as iron, steel, tiles, bricks, natural stone, concrete, lime silicate bricks, marble, floor tiles, artificial stone, flat glass, hollow glass, laminated glass, bridges, roofs, facades, to name but a few.

In addition, the siloxane mixtures prepared by the present invention can be used for waterproofing and surface modification of textiles, leather, cellulose and starch products, for coating glass and mineral fibers, for example as binding agents or as additives to binding agents, for surface modification of fillers, for improving the rheological properties of dispersions and emulsions, as adhesion promoters, for example, for improving the adhesion of organic polymers on inorganic substrates, as release agents, as crosslinkers or as additives for coatings and paints.

Having now generally described this invention, a further understanding can be obtained by reference to certain specific examples which are provided herein for purposes of illustration only and are not intended to be limiting unless otherwise specified.

EXAMPLES

Example 1

Continuous Manufacture of an n-propylethoxysiloxane Mixture (VPS 9892)

A schematic of the apparatus employed in the practice of the present invention is shown in the FIGURE and the system components are identified as follows:

1 alcohol reservoir which is a 2 liter glass flask,
2 chlorosilane reservoir (mixture) in a 1 liter glass flask,
3 return alcohol reservoir which is a 100 liter drip funnel,
4 reactor which is a 2 liter double-sheathed flask, oil thermostat heated,
5 column bottom which is a 2 liter double-sheathed flask, oil thermostat heated,
6 column of a length of 150 cm, a diameter of 28 mm and filled with porcelain saddles of a diameter of about 4 mm,
7 an intensive cooler of a length of 55 cm,
8 a deep cooler of a length of 20 cm, cooled with dry ice/isopropanol mixture,
9 a preheater of a double-sheathed glass vessel with V=of about 40 ml, oil thermostat heated,
10 an evaporator of a double-sheathed glass vessel with V=of about 20 ml, oil thermostat heated, and
11 a water/alcohol mixture reservoir which is a 500 ml glass flask.

The five pumps 21, 23, 25, 27 and 29 in the system are all PROMINENT diaphragm pumps "Gamma/4", wherein pumps 21, 23 and 27 have a dosing output of 0.69 liter/h, pump 25 has a dosing output of 1.60 liter/h, and pump 29 has a dosing output of 0.2 liter/h.

Temperature control at places in the apparatus requiring temperature control are the:

T heating circuit (HC) for reactor: 70° C.; T (reactor) ca. 50° C.

T HC evaporator: 150° C.; T (evaporator) ca. 120° C.

T HC column bottom+$1^{st}$ charge: 180° C.; T (column bottom) ca. 160° C.

T HC $2^{nd}$ a+$3^{rd}$ charge: 100° C.; T (on $3^{rd}$ column charge) ca. 89° C.

T HC preheater: 50° C.

Description of the Process

Chlorosilanes, together with water and reflux ethanol are metered (heated and stirred) in prescribed quantities into the reactor 4. Metering from the reactor via the preheater 9 to the column is adjusted such that there is a quantity of fluid of ca. 25 to 200 ml in the reactor 4. At the same time ethanol is supplied via the evaporator 10 in the prescribed amount to the lower section of the column 6. The resulting waste gas (HCl) is withdrawn. Excess ethanol and chlorosilanes (including chloroalkoxysilanes and chloroalkoxysiloxanes as well as dissolved HCl) are condensed and conveyed to the reactor 4 as reflux ethanol. Product is removed continuously from the column bottom 5, so that a constant liquid level is maintained in the column bottom 5.

Educts
PTCS (n-propyltrichlorosilane, purity=99.3 area-%)
Distilled water (purity=98.5 area-%)
Dose PTCS: approx. 1.45–1.65 mol/h
ethanol: approx. 2.2–3.4 mol/h
recycled ethanol: approx. 3.0–3.4 mol/h
distilled water: approx. 0.98–1.28 mol/h Secondary Treatment The product still contains minimal quantities of chloride, for example in the form of n-propylethoxychlorosiloxanes. The addition of the stoichiometric quantity of ethanolic caustic soda solution to the product leads to precipitation of NaCl that can be filtered through a pressure nutsche. Excess ethanol is separated at the rotation evaporator. This effectively increases the flash point of the product.

Characterizing the Product (Values in Brackets Without Secondary Treatment)

flash point: 89° C. (40° C.)
$SiO_2$ content: 41.3% w/w
viscosity: 4.8 mPa s
hydrolysable chloride: <10 ppm (461 mg/kg)
color index: 10 Apha

Example 2

Continuous Manufacture of a Vinylethoxysiloxane Mixture (DS 6498)

The apparatus employed in the description of Example 1 was employed.

Temperature control:
T heating circuit (HC) for reactor: 70° C.; T (reactor) ca. 50° C.
T HC evaporator: 150° C.; T (evaporator) ca. 120° C.
T HC column bottom+$1^{st}$ charge: 180° C.; T (column bottom) ca. 160° C.
T HC $2^{nd}$+$3^{rd}$ charge: 100° C.; T (on $3^{rd}$ column charge) ca. 87° C.
T HC preheater: 50° C.

Description of the Process

The same procedure as described in Example 1 was used with the following difference:
Educts VTCS (vinyltrichlorosilane, purity=99.1 area-%)
ethanol (purity=98.5 area-%) distilled water (is added in mixture 1:1 with ethanol)

Dose

VTCS: approx. 1.4 mol/h
ethanol: approx. 1.8 mol/h
recycled ethanol: approx. 3.4 mol/h
distilled water: approx. 1.25 mol/h Secondary Treatment The product still contains minimal quantities of chloride, for example in the form of vinylethoxychlorosiloxanes. The addition of the stoichiometric quantity of ethanolic caustic soda solution leads to precipitation of NaCl that can be filtered through a pressure nutsche. Excess ethanol is separated at the rotation evaporator. This effectively increases the flash point of the product.

Characterization of the product (without secondary treatment)

| | |
|---|---|
| $SiO_2$: | 47.1% |
| viscosity: | 4.9 mPa s |
| hydrolysable chloride: | 18 mg/kg |
| color index: | 45 |
| density: | 1.030 g/cm³ |

Example 3

Continuous Synthesis of a n-propylvinylethoxysiloxane Cocondensate (DS 6598)

The apparatus employed in the description of Example 1 was employed.

Temperature Control:

T heating circuit (HC) for reactor: 70° C.; T (reactor) ca. 50° C.
T HC evaporator: 150° C.; T (evaporator) ca. 112° C.
T HC column bottom+$1^{st}$ charge: 180° C.; T (column bottom) ca. 168° C.
T HC $2^{nd}$+$3^{rd}$ charge: 100° C.; T (on $3^{rd}$ column charge) ca. 85° C.
T HC preheater: 50° C.

Description of the Process

The same procedure as described in Example 1 was used with the following difference:
Educts VTCS (vinyltrichlorosilane, purity=99.1 area-%)
PTCS (n-propyltrichlorosilane, purity=99.3 area-%)
ethanol (purity=98.5 area-%)
distilled water (is added in mixture 1:1 with ethanol)
VTCS and PTCS are added in mixture, molar mixture ratio: 1 mol VTCS: 0.95 mol PTCS Dose chlorosilane mixture: approx. 2.0 mol/h
ethanol: approx. 3.0 mol/h
recycled ethanol: approx. 4.5 mol/h
distilled water: approx. 1.65 mol/h Secondary Treatment The product still contains minimal quantities of chloride, for example in the form of vinyl/n-propylethoxychlorosiloxanes. The addition of the stoichiometric quantity of ethanolic caustic soda solution leads to precipitation of NaCl, which can be filtered through a pressure nutsche. Excess ethanol is separated at the rotation evaporator. This effectively increases the flash point of the product.

Characterization of the Product (without secondary treatment)

| SiO$_2$: | 43.2% |
|---|---|
| viscosity: | 4.1 mPa s |
| hydrolysable chloride: | 163 mg/kg |
| color index: | 15 |
| free ethanol: | 0.7% by weight |
| density: | 0.995 g/cm$^3$ |

The disclosure of German priority application Serial No. 10056343.0 filed Nov. 14, 2000, is hereby incorporated by reference into the present application.

Obviously, numerous modifications and variations of the present invention are possible in light of the above teachings. It is therefore to be understood that within the scope of the appended claims, the invention may be practiced otherwise than as specifically described herein

What is claimed as new and is intended to be secured by Letters Patent is:

1. A process for the continuous manufacture of a mixture of organosiloxanes of formula I:

wherein R and R" are identical or different and are methyl, ethyl, vinyl, n-propyl, i-propyl, γ-chloropropyl, n-butyl, n-pentyl, i-pentyl, n-hexyl, i-hexyl, n-heptyl, i-heptyl, n-octyl, i-octyl, hexadecyl, octadecyl or alkoxy, R' represents methyl or ethyl, n and m are identical or different and each is 0 or an integer ranging from 1 to 20, on the condition that (n+m)≧2, y and y' are >0 to 1.5, z and z' are 0 to <3, wherein y and y' and z and z' are the same or different, and (2y+z)=3 and (2y'+z')=3, comprising:
reacting in a first stage the constituents of (i) an organotrichlorosilane or a mixture of organotrichlorosilanes, or a mixture of at least one organotrichlorosilane and tetrachlorosilane, (ii) water and (iii) alcohol, combined in a molar ratio (i):(ii):(iii) of 1:(0.59 to 0.95):(0.5 to 100), at a temperature of 0 to 150° C., which produces hydrogen chloride and a crude organoalkoxysiloxane as products which are removed from the system;
proportionately transferring the crude organoalkoxysiloxane product to a reaction distillation column of a subsequent second stage after an average dwell time of 0.5 to 180 minutes; and
conducting reaction and distillation in said reaction distillation column in which volatile constituents are withdrawn from the top of the column and the organoalkoxysiloxane product is withdrawn as a bottom product, wherein the reaction-distillation column is operated at a bottom temperature of 50 to 200° C.

2. The process as claimed in claim 1, wherein said organotrichlorosilane is methyltrichlorosilane, vinyltrichlorosilane, ethyltrichlorosilane, n-propyltrichlorosilane, i-propyltrichlorosilane, γ-chloropropyltrichlorosilane, i-butyltrichlorosilane, n-butyltrichlorosilane, pentyltrichlorosilane, hexyltrichlorosilane, heptyltrichlorosilane, n-octyltrichlorosilane, i-octyltrichlorosilane, hexadecyltrichlorosilane or octadecyltrichlorosilane.

3. The process as claimed in claim 1, wherein methanol or ethanol is alcohol (iii).

4. The process as claimed in claim 1, wherein the constituents (i), (ii) and (iii) are present in a molar ratio of 1:(≧0.6 to 0.9):(1 to 3).

5. The process as claimed in claim 1, wherein, after an average dwell time of 1 to 60 minutes, the crude product is transferred proportionately from the first process stage to the reaction-distillation column of the second stage.

6. The process as claimed in claim 1, wherein the crude product is conveyed from the first process stage via a preheater before introduction to the second stage.

7. The process as claimed in claim 1, wherein the crude product is conveyed from the first process stage to the upper half of the reaction-distillation column.

8. The process as claimed in claim 1, wherein alcohol in a molar ratio of constituents (i):(iii) of 1:0.1 to 100 is supplied to the lower section of the reaction-distillation column of the second process stage.

9. The process as claimed in claim 1, wherein the alcohol fraction which accumulates in the second process stage at the top of the column is fed back to the reaction-distillation column of the second process stage and/or to the first process stage.

10. A process for the continuous manufacture of a mixture of organosiloxanes, comprising:
reacting in a first stage the constituents of (i) RSiCl$_3$ or R"SiCl$_3$, wherein R and R" are identical or different and are methyl, ethyl, vinyl, n-propyl, i-propyl, γ-chloropropyl, n-butyl, n-pentyl, i-pentyl, n-hexyl, i-hexyl, n-heptyl, i-heptyl, n-octyl, i-octyl, hexadecyl, octadecyl or alkoxy, or a combination of these two organotrichlorosilanes or a mixture of at least one of the organotrichlorosilanes and tetrachlorosilane, (ii) water and (iii) methanol or ethanol, combined in a molar ratio (i): (ii): (iii) of 1: (0.59 to 0.95): (0.5 to 100), at a temperature of 0 to 150° C., which produces hydrogen chloride and a crude organoalkoxysiloxane as products which are removed from the system;
proportionately transferring the crude organoalkoxysiloxane product to a reaction distillation column of a subsequent second stage after an average dwell time of 0.5 to 180 minutes; and
conducting reaction and distillation in said reaction distillation column in which volatile constituents are withdrawn from the top of the column and the organoalkoxysiloxane product is withdrawn as a bottom product, wherein the reaction-distillation column is operated at a bottom temperature of 50 to 200° C.

11. A mixture of linear, cyclic and/or net-like organoalkoxysiloxanes, which is prepared by the process as claimed in claim 10.

12. A method of treating organic or inorganic surfaces, comprising:
applying to said organic or inorganic surfaces the mixture of organoalkoxysilanes as claimed in claim 11 as a concentrate, in diluted form, in emulsified form or a component of a surface treatment agent.

13. The method as claimed in claim 12, wherein the treatment is applied on inorganic surfaces, for water-, oil-, dirt and/or dye-repellency, for corrosion inhibition or for adhesion-promotion of metals, ceramics, artificial stones, glass, building materials, building components and buildings; for waterproofing and surface modification of textiles, leather, cellulose and starch products; for coating glass and mineral fibers or for surface modification of fillers.

14. A method of improving the rheological properties of dispersions and emulsions, comprising:

incorporating the mixture linear, cyclic and/or net-like organoalkoxysiloxanes of claim 11 in a dispersion or emulsion.

15. A coating or paint formulation, comprising:
a paint or coating formulation containing the mixture of linear, cyclic and/or net-like organoalkoxysiloxanes of claim 11.

16. A binding agent, comprising:
the mixture of linear, cyclic and/or net-like organoalkoxysiloxanes of claim 11 alone or as a component of a binding agent formulation.

17. A release agent, comprising:
the mixture of linear, cyclic and/or net-like organoalkoxysiloxanes of claim 11 as a release agent.

18. A adhesion promoter, comprising:
the mixture of linear, cyclic and/or net-like organoalkoxysiloxanes of claim 11 as an adhesion promoter.

19. A cross-linking agent, comprising:
the mixture of linear, cyclic and/or net-like organoalkoxysiloxanes of claim 11 as the cross-linking agent.

20. A process for the continuous manufacture of a mixture of organosiloxanes, comprising:
reacting in a first stage the constituents of (i) $RSiCl_3$ or $R''SiCl_3$, wherein R and R'' are identical or different and are methyl, ethyl, vinyl, n-propyl, i-propyl, γ-chloropropyl, n-butyl, n-pentyl, i-pentyl, n-hexyl, i-hexyl, n-heptyl, i-heptyl, n-octyl, i-octyl, hexadecyl, octadecyl or alkoxy, or a combination of these two organotrichlorosilanes or a mixture of at least one of the organotrichlorosilanes and tetrachlorosilane, (ii) water and (iii) methanol or ethanol, combined in a molar ratio (i):(ii):(iii) of 1: (0.59 to 0.95):(0.5 to 100), at a temperature of 0 to 150° C., which produces hydrogen chloride and a crude organoalkoxysiloxane as products which are removed from the system;

conveying the crude organoalkoxysiloxane product obtained to a preheater;

proportionately transferring the preheated crude organoalkoxysiloxane product to a reaction distillation column of a subsequent second stage after an average dwell time of 0.5 to 180 minutes; and conducting reaction and distillation in said reaction distillation column in which volatile constituents are withdrawn from the top of the column and the organoalkoxysiloxane product is withdrawn as a bottom product, wherein the reaction-distillation column is operated at a bottom temperature of 50 to 200° C.

* * * * *